United States Patent [19]

Kleschick et al.

[11] Patent Number: 4,650,892

[45] Date of Patent: Mar. 17, 1987

[54] PROCESS FOR THE PREPARATION OF HERBICIDAL SULFONAMIDES

[75] Inventors: William A. Kleschick, Martinez; Anna P. Vinogradoff, Concord, both of Calif.; Joseph E. Dunbar, Midland, Mich.

[73] Assignee: The Dow Chemical Company, Midland, Mich.

[21] Appl. No.: 812,613

[22] Filed: Dec. 23, 1985

Related U.S. Application Data

[62] Division of Ser. No. 691,331, Jan. 14, 1985.

[51] Int. Cl.$^4$ .................. C07D 487/00; C07D 239/00; C07D 249/14; C07C 157/14
[52] U.S. Cl. ........................................ 558/5; 544/263; 544/251; 548/267

[58] Field of Search ............... 558/4, 5; 544/250, 251, 544/263; 549/61, 62, 63, 64, 65

[56] References Cited

U.S. PATENT DOCUMENTS 4,328,247  5/1982  Drabek et al. ........................... 558/4

*Primary Examiner*—Henry R. Jiles
*Assistant Examiner*—Robert C. Whittenbaugh
*Attorney, Agent, or Firm*—Merlin B. Davey

[57] ABSTRACT

Sulfonamides derived from substituted 2-amino-1,2,4-triazolo[1,5-a]pyrimidines are prepared by reacting a desired sulfonamide with dimethyl N-cyanodithioiminocarbonate in the presence of a base followed by reaction with an excess of hydrazine and then a 1,3-dicarbonyl compound.

The resulting products have a variety of herbicidal uses.

5 Claims, No Drawings

PROCESS FOR THE PREPARATION OF HERBICIDAL SULFONAMIDES

CROSS-REFERENCE TO RELATED APPLICATION

This is a divisional of application Ser. No. 691,331, filed Jan. 14, 1985, pending.

BACKGROUND OF THE INVENTION

Compounds of general structure I

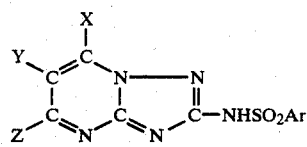

wherein Ar represents an aromatic (substituted or unsubstituted) or heteroaromatic (substituted or unsubstituted) ring system exhibit herbicidal activity against a variety of weed species.

While some of the compounds in this family may be prepared by a conventional, convergent approach via the requisite substituted 2-amino-1,2,4-triazolo [1,5-a]pyrimidine, as described in copending application Ser. No. 574,232 filed Jan. 26, 1984, many analogs cannot be made following this approach. The highly insoluble nature of many of the appropriate substituted 2-amino-1,2,4-triazolo[1,5-a]pyrimidines prohibit their reaction with the less reactive and less stable aromatic sulfonyl chlorides.

SUMMARY OF THE INVENTION

We have found a new method for the preparation of compounds of type I which eliminate most of the limitations of methodology which had been previously described. The new method of this invention also provides novel intermediates as described more fully hereinafter.

DETAILED DESCRIPTION OF THE INVENTION

The novel procedure for the preparation of compounds of formula I is illustrated in Scheme I. The starting aromatic sulfonyl chlorides II and sulfonamide III are commercially available or may be prepared as described in copending application Ser. No. 574,232 filed Jan. 26, 1984, which is incorporated herein by reference. In accordance with this invention the sulfonamides III are reacted with dimethyl N-cyanodithioiminocarbonate in the presence of a base in a solvent. Bases which are effective in this transformation include tertiary amine (i.e. triethylamine) or alkali metal hydroxides, alkoxides or carbonates (i.e. NaOH, NaOCH$_3$ or K$_2$CO$_3$). Appropriate solvents include acetone, methyl ethyl ketone acetonitrile or tetrahydrofuran (THF). The reaction may be run at temperatures ranging from ambient temperature to reflux. The products of this transformation (IV) may be isolated directly as their salts and converted to their neutral species by acidification. In some instances the salt may be used directly in subsequent transformations without purification or conversion to the corresponding neutral species. Compound IV may be reacted with an excess of hydrazine to form the intermediate 1,2,4-triazoles V. This reaction is generally carried out in solvents such as acetonitrile, THF, DMF, or DMSO at ambient temperature although higher temperatures may be employed to increase the rate of reaction. The amount of excess hydrazine utilized in this transformation range from 5 to 400 mole percent. The final step in this sequence for the conversion of compound V to I may be carried out as generally outlined in "Heterocyclic Systems with Bridgehead Nitrogen Atoms", Part Two, W. L. Mosby, Interscience Publishers, 1961, p. 878. A wide variety of 1,3-dicarbonyl compounds may be used in this reaction which may be run under acidic (i.e. acetic acid as a solvent), neutral (i.e. DMF as a solvent) or basic conditions (i.e. using alkali metal alkoxides or carbonates in polar aprotic solvents such as DMF or DMSO).

Scheme I

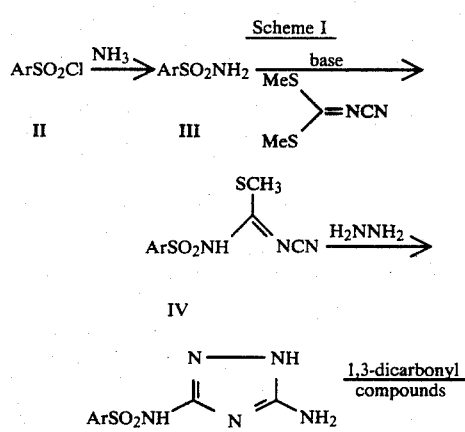

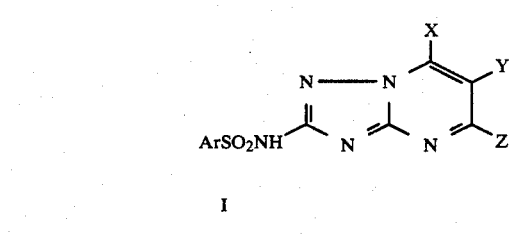

In examples where unsymmetrical 1,3-dicarbonyl compounds are employed in the process outlined in Scheme I, the possibility of obtaining two different isomeric condensation products exists. Often the appropriate choice of reaction conditions (i.e. acidic or basic) allows for control of the regiochemistry of the annulation process.

In cases where β-ketoesters or malonic esters are used in the last step of the process described above, the products contain hydroxy groups (i.e. I where X and/or Z is OH). These products may be subjected to further transformations involving conversion of the hydroxy groups to chlorine with phosphorous oxychloride. The resulting halo substituted compounds are capable of undergoing reaction with nucleophiles to affect nucleophilic substitution of the halogen. This procedure is highly useful in the preparation of alkoxy, alkylthio and amino substituted heterocyclic ring systems.

An alternative procedure for the synthesis of intermediates of general structure IV is illustrated in equation 1. The starting materials (VI) may be prepared from aromatic sulfonamides by known art (i.e. F. L. Merchan, *Synthesis*, 984 (1982); R. Gompper, et al., *Chem. Ber.*, 99, 2885, 2990 (1966)). These intermediates may be reacted with cyanamide in the presence of base. Bases include tertiary amines and alkali metal alkoxides, hydroxides and carbonates. This reaction is most frequently carried out in acetonitrile or THF at temperatures ranging from ambient temperature to reflux.

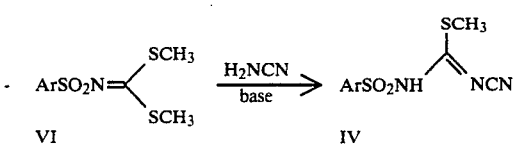

In certain instances intermediates VI may convert to their corresponding mono or dichloro derivatives (i.e. VII and VIII respectively). This may be accomplished by known art (i.e. E. Kuhle, et al., *Angew, Chem Int. Ed. Engl.*, 6, 649 (1967)). These intermediates may then be advantageously used in a manner analogous to VI in the synthesis of compounds of general structure I.

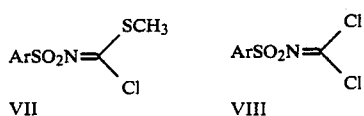

Compounds advantageously prepared by the process of this invention have the general formula:

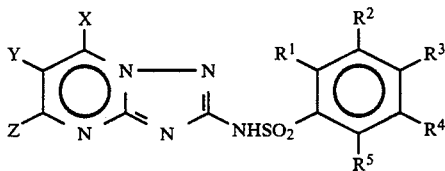

wherein $R^1$ represents halo (F, Cl, Br, I), $-NO_2$, phenyl, OAr, $-CF_3$, $-OCF_3$, $-OCF_2CF_2H$, $-OCF_2CCl_2H$, $-OCH_2CF_3$, $-SCF_3$, $-SCF_2CF_2H$, $-SCF_2CCl_2H$, $-SOCF_3$, $-SOCF_2CF_2H$, $-SOCF_2CCl_2H$, $-SO_2CF_3$, $-SO_2CF_2CF_2H$, $-SO_2CF_2CCl_2H$, $-SR^6$, $-SOR^6$, $-SO_2R^6$, $-CN$, $-COOR^7$, $-CONH_2$, $-CONHR^8$, $-CONR^8(R^9)$, $-SO_3R^8$ and $-SO_3CH_2CF_3$; $R^2$ and $R^4$ represent H, halo (F, Cl, Br, I), $C_1$–$C_4$ alkyl, $COOR^7$ and $-OR^8$; $R^3$ is H; and $R^5$ represents H, $C_1$ to $C_4$ alkyl, halo (F, Cl, Br, I), $NO_2$, $CF_3$, $-OCF_3$, $-OCF_2CF_2H$, $-OCF_2CCl_2H$, $-OCH_2CF_3$, $-SCF_3$, $-SCF_2CF_2H$, $-SCF_2CCl_2H$, $-SOCF_3$, $-SOCF_2CF_2H$, $-SOCF_2CCl_2H$, $-SO_2CF_3$, $-SO_2CF_2CF_2H$, $-SO_2CF_2CCl_2H$, $-SR^6$, $-SOR^6$, $-SO_2R^6$, $-CN$, $-COOR^7$, $-CONH_2$, $-CONHR^8$, $-CONR^8(R^9)$, $-SO_3R^8$, $-SO_3CH_2CF_3$, $-CR^6R^6OR^6$ and $-CR^6R^6SR^6$ wherein Ar represents substituted or unsubstituted aryl or substituted or unsubstituted heteroaryl, $R^6$ represents H, aryl or $C_1$–$C_4$ alkyl, $R^7$ represents $C_1$–$C_6$ alkyl, alkenyl, alkynyl, aryl, substituted alkyl or substituted aryl and $R^8$ and $R^9$ individually represent $C_1$–$C_4$ alkyl; and X, Y and Z represent H, $C_1$–$C_4$ alkyl, $C_1$–$C_4$ alkoxy halo (F, Cl, Br, I), or X and Y or Y and Z can be joined to form a cycloalkyl ring (i.e., $-(CH_2)_n-$ wherein n is 3 or 4) or X and Y or Y and Z can be joined to form a ring containing a heteroatom (i.e., $-O(CH_2)_n-$ wherein n is 2 or 3). In this specification aryl and heteroaryl refer to 5- or 6-membered aromatic or heteroaromatic ring systems.

The following examples serve to illustrate the invention.

EXAMPLE 1

N'-Cyano-N-(2-nitrophenylsulfonyl)-S-methylisothiourea

A mixture of 2.02 g (10.0 mmol) of 2-nitrobenzenesulfonamide, 1.46 g (10.0 mmol) of dimethyl N-cyanodithioiminocarbonate and 1.38 g (10.0 mmol) of powdered, anhydrous $K_2CO_3$ in 16 ml of acetone was heated at reflux for 20 hours. The reaction mixture was filtered and the solid collected was washed several times with acetone. The filtrate was evaporated and the orange oily residue was triturated with ether to afford a solid. The solid was collected by filtration, washed with ether and suspended in 10 ml of $^1$N HCl. After stirring for 1 hour the solid was collected by filtration, washed with water and dried to yield 1.65 g (55 percent) of the desired product as a cream colored solid, mp 122° C. (decomposition). IR and $^1$H NMR spectra were consistent with the assigned structure.

Analysis: Calculated for $C_9H_8N_4O_4S_2$: C, 36.00; H, 2.69; N, 18.66; S, 21.35. Found: C, 36.10; H, 2.74; N, 18.72; S, 21.22.

EXAMPLE 2

N-(5-Amino-1,2,4-triazol-3-yl)-2-nitrobenzenesulfonamide

A suspension of 29.4 g (98.0 mmol) of N'-Cyano-N-(2-nitrophenylsulfonyl)-S-methylisothiourea in 100 ml of acetonitrile was treated with 6.2 ml (6.3 g, 0.20 mol) of anhydrous hydrazine. A mild exothermic reaction occurred as the reaction mixture became homogeneous. After stirring for 9 days the precipitated solid was collected by filtration and dried to afford 22.9 g of yellow solid. The crude product was recrystallized from HOAc to yield a total of 15.9 g (57 percent) of the desired product as a pale yellow solid, mp 255°–256° C. IR and $^1$H NMR spectra were consistent with the assigned structure.

Analysis: Calculated for $C_8H_8N_6O_4S$: C, 33.80; H, 2.84; N, 29.57; S, 11.28. Found: C, 34.11; H, 2.79; N, 29.35; S, 11.50.

EXAMPLE 3

N-(5,7-dimethyl-1,2,4-triazolo[1,5-a]-pyrimidin-2-yl)-2-nitrobenzenesulfonamide

A mixture of 2.43 g (9.00 mmol) of N-(5-amino-1,2,4-triazol-3-yl)-2-nitrobenzenesulfonamide and 1.85 ml (1.80 g, 18.0 mmol) of 2,4 pentanedione in 25 ml of glacial acetic acid was heated at reflux for 19 hours. After cooling to room temperature, the solid which separated was collected by filtration, washed with acetic acid and dried in vacuo to yield 2.58 g (82 percent) of the desired product as an off-white crystalline solid, mp 255°–256° C. IR and $^1$H NMR spectra were in agreement with the assigned structure.

Analysis: Calculated for $C_{13}H_{12}N_6O_4S$: C, 44.83; H, 3.47; N, 24.13; S, 9.20. Found: C, 44.88; H, 3.34; N, 24.51; S, 9.09.

EXAMPLE 4

N'-Cyano-N-(2,5-dichlorophenylsulfonyl)-S-methylisothiourea

A solution of 10.6 g (43.2 mmol) of 2,5-dichlorobenzenesulfonamide, 7.15 g (44.0 mmol) of 90 percent dimethyl N-cyanodithioiminocarbonate and 1.8 g (44 mmol) of NaOH in 60 ml of ethanol and 10 ml of $H_2O$ was heated at reflux for 6 hours. After cooling to room temperature the reaction mixture was poured into 600 ml of ice water. The resulting solution was acidified with 6N HCl to separate 2.2 g of the desired product as a white solid. Concentration of the filtrate gave an additional 8.5 g of the desired product. The total yield of material was 10.7 g (76 percent) of white solid, mp 145° C. IR and $^1$H NMR spectra were consistent with the assigned structure.

Analysis: Calculated for $C_9H_7Cl_2N_3O_2S_2$: C, 33.34; H, 2.18; N, 12.96. Found: C, 33.50; H, 2.39; N, 12.82.

EXAMPLE 5

N-(5-Amino-1,2,4-triazol-3-yl)-2,5-dichlorobenzenesulfonamide

A mixture of 8.51 g (26.2 mmol) of N'-cyano-N-(2,5-dichlorophenylsulfonyl)-S-methylisothiourea and 10 ml (10 g, 0.20 mol) of hydrazine monohydrate in 85 ml of ethanol was heated at reflux for 30 minutes. After cooling to room temperature, the solid which separated was collected and suspended in 170 ml of $H_2O$ and the suspension was acidified with concentrated aqueous HCl. After stirring the suspension for 4 hours the solid was collected and dried in vacuo to yield 5.10 g (57 percent) of the desired product as a hydrochloride salt, mp 306°–308° C. IR and $^1$H NMR spectra were consistent with the assigned structure.

Analysis: Calculated for $C_8H_7Cl_2N_5O_2S·HCl$: C, 27.88; H, 2.34; N, 20.32. Found: C, 28.36; H, 2.50; N, 19.78.

EXAMPLE 6

N-(5,7-dimethyl-1,2,4-triazolo[1,5-a]-pyrimidin-2-yl)-2,5-dichlorobenzenesulfonamide A solution of 4.60 g (13.3 mmol) of N-(5-amino-1,2,4-triazol-3-yl)-2,5-dichlorobenzenesulfonamide hydrochloride and 4.0 g (40 mmol) of 2,4-pentanedione in 60 ml of glacial acetic acid was heated at reflux for 4 hours. The reaction mixture was cooled to room temperature and poured into 500 ml of ice water to separate a solid. The solid was collected by filtration and dried to yield 4.53 g (92 percent) of the desired product as a white solid, m.p. 216.5°–218.5° C.

Analysis: Calculated for $C_{13}H_{11}Cl_2N_5O_2S$: C, 41.95; H, 2.98; N, 18.81. Found: C, 41.83; H, 3.10; N, 18.67.

EXAMPLE 7

2-Chloro-N-(5-methyl-7-trifluoromethyl-1,2,4-triazolo[1,5-a]pyrimidin-2-yl)benzenesulfonamide A mixture of 2.19 g (8.00 mmol) of N-(5-amino-1,2,4-triazol-3-yl)-2-chlorobenzenesulfonamide and 1.09 ml (1.38 g, 8.96 mmol) of 1,1,1-trifluoro-2,4-pentanedione in 9 ml of glacial acetic acid was heated at reflux for 21 hours. After cooling to room temperature, the reaction mixture was poured into a mixture of ice and water. The solid which separated was collected by filtration, washed with water and dried to yield 2.90 g (93 percent) of the desired product as a white solid, mp 203°–204.5° C. IR and $^1$H NMR spectra were in agreement with the assigned structure.

Analysis: Calculated for $C_{13}H_9ClF_3N_5O_2S$: C, 39.86; H, 2.32; H, 17.88; Cl, 9.05; S, 8.18. Found: C, 40.23; H, 2.31; N, 18.22; Cl, 9.13; S, 8.26.

EXAMPLE 8

2-Chloro-N-(7-methyl-1,2,4-triazolo[1,5-a]pyrimidin-2-yl)benzenesulfonamide

A sample of 3.0 ml (2.7 g, 20 mmol) of acetylacetaldehyde dimethylacetal was added to a solution of 2.74 g (10.0 mmol) of N-(5-amino-1,2,4-triazol-3-yl)-2-chlorobenzenesulfonamide in 20 ml of glacial acetic acid at reflux over 12 hours. After the addition was complete the reaction mixture was heated at reflux for 15 hours and cooled to room temperature. The solid which separated was collected by filtration, washed with acetic acid and dried to yield 1.92 g (59 percent) of the desired product as white solid, mp 267.5°–269° C. IR and $^1$H NMR spectra were in agreement with the assigned structure.

Analysis: Calculated for $C_{12}H_{10}ClN_5O_2S$: C, 44.52; H, 3.11; N, 21.63; Cl, 10.95; S, 9.90. Found: C, 44.36; H, 3.07; N, 21.69; Cl, 10.82; S, 10.15.

EXAMPLE 9

2-Chloro-N-(1,2,4-triazolo[1,5-a]-pyrimidin-2-yl)benzenesulfonamide

A mixture of 2.74 g (10.0 mmol) of N-(5-amino-1,2,4-triazol-3-yl)-2-chlorobenzenesulfonamide and 3.3 ml (3.3 g, 20 mmol) of malonaldehyde bis(dimethylacetal) in 10 ml of glacial acetic acid was heated at reflux for 24 hours. After cooling to room temperature, the solid which separated was collected by filtration, washed with acetic acid and dried to yield 1.78 g (58 percent) of the desired product as a tan solid, mp 253.5°–256.5° C. IR and $^1$H NMR spectra were in agreement with the assigned structure.

Analysis: Calculated for $C_{11}H_8ClN_5O_2S$: C, 42.66; H, 2.60; N, 22.61; Cl, 11.45; S, 10.35. Found: C, 42.97; H, 2.60; N, 22.42; Cl, 11.19; S, 10.07.

EXAMPLE 10

2-Chloro-N-(6-Chloro-1,2,4-triazolo[1,5-a]pyrimidin-2-yl)benzenesulfonamide

A mixture of 2.46 g (9.00 mmol) of N-(5-amino-1,2,4-triazol-3-yl)-2-chlorobenzenesulfonamide and 1.67 g (9.90 mmol) of mucochloric acid in 20 ml of DMF was heated to reflux for 16.5 hours. After cooling to room temperature, the solvent was removed by evaporation at reduced pressure and the residue was treated with 20 ml of 0.5N NaOH. After stirring vigorously for ~30 minutes the mixture was filtered through celite and the filtrate was acidified with 2N HCl. The solid which separated was collected by filtration, washed with water and recrystallized from acetic acid—water to yield 0.70 g (23 percent) of the desired product as a light brown solid, mp 256.5°–260.5° C. IR and $^1$H NMR spectra were in agreement with the assigned structure.

Analysis: Calculated for $C_{11}H_7Cl_2N_5O_2S$: C, 38.39; H, 2.05; N, 20.35; Cl, 20.60; S, 9.32. Found: C, 38.74; H, 2.08; N, 20.84; Cl, 19.54; S, 8.70.

EXAMPLE 11

2-Chloro-N-(6-methyl-1,2,4-triazolo[1,5-a]pyrimidin-2-yl)benzenesulfonamide

A mixture of 2.02 g (8.36 mmol) of 1,3-bis(dimethylamino)-2-methyltrimethinium perchlorate and 2.29 g (8.36 mmol) of N-(5-amino-1,2,4-triazol-3-yl)-2-chlorobenzenesulfonamide in 25 ml of glacial acetic acid was heated at reflux for 19 hours. The solvent was removed by evaporation at reduced pressure, and the residue was treated with 20 ml of 0.5N NaOH. Some additional 1N NaOH was added to dissolve all of the material (~pH 10). The solution was filtered and the filtrate was acidified with 2N HCl to precipitate a solid. The solid was collected by filtration, washed with water and dried to yield 2.34 g (87 percent) of the desired product as a pale yellow solid, mp 236°–239° C. IR and $^1$H NMR spectra were in agreement with the assigned structure.

Analysis: Calculated for $C_{12}H_{10}ClN_5O_2S$: C, 44.52; H, 3.11; N, 21.63; Cl, 10.95; S, 9.90. Found: C, 44.17; H, 3.05; N, 21.93; Cl, 11.01; S, 9.69.

EXAMPLE 12

N-(5-Amino-1,2,4-triazol-3-yl)-2,6-dichlorobenzenesulfonamide

A mixture of 90.1 g (0.398 mol) of 2,6-dichlorobenzenesulfonamide, 64.7 g (0.398 mol) of dimethyl N-cyanodithioiminocarbonate and 58.3 g (0.420 mol) of powdered anhydrous $K_2CO_3$ in 800 ml of THF was heated at reflux for 3 hours. After cooling to 30° C., 25.3 ml (25.6 g, 0.798 mol) of anhydrous hydrazine was added dropwise over 30 minutes. The resulting mixture was stirred for 3 days at ambient temperature and filtered. The solid collected was washed with THF, suspended in 400 ml of water and acidified with 180 ml of acetic acid. The resulting mixture was filtered, and the solid collected was washed with water and dried to yield 112 g (91 percent) of the desired product as a white solid, mp 300° C. (decomp.) IR and $^1$H NMR spectra were in agreement with the assigned structure.

Analysis: Calculated for $C_8H_7Cl_2N_5O_2S$: C, 31.18; H, 2.29; N, 22.73; Cl, 23.01; S, 10.40. Found: C, 31.39; H, 2.26; N, 22.70; Cl, 22.88; S, 10.25.

Following the above general procedures and employing appropriate starting materials the compounds indicated in the tables were prepared.

TABLE I

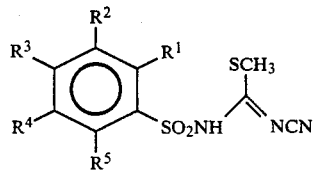

| $R^1$ | $R^2$ | $R^3$ | $R^4$ | $R^5$ | Physical Properties | Elemental Composition | C | H | N | Cl | S |
|---|---|---|---|---|---|---|---|---|---|---|---|
| H | H | H | H | H | mp 122° C. (decomp.) | Exact mass calcd. for $C_9H_9N_3O_2S_2$: 255.0136 Found: 255.0125 | | | | | |
| $NO_2$ | H | H | H | H | mp 122° C. (decomp.) | Anal. Calcd. for $C_9H_8N_4O_4S_2$: Found: | 36.00 36.10 | 2.69 2.74 | 18.66 12.95 | — — | 21.35 21.22 |
| $CF_3$ | H | H | H | H | mp 128° C. (decomp.) | Anal. Calcd. for $C_{10}H_8F_3N_3O_2S_2$: Found: | 37.15 37.02 | 2.49 2.55 | 13.00 12.95 | — — | 19.83 20.00 |
| Cl | H | H | H | H | mp 126.5° C. (decomp.) | Anal. Calcd. for $C_9H_8ClN_3O_2S_2$: Found: | 37.31 37.15 | 2.78 2.82 | 14.50 14.67 | 12.24 12.40 | 22.13 21.90 |
| $CH_3$ | H | H | H | H | mp 129° C. (decomp.) | Exact mass calcd. for $C_{10}H_{11}N_3O_2S_2$: 269.0292 Found: 269.0299 | | | | | |
| H | H | $CH_3$ | H | H | mp 137.5–139° C. (decomp.) | Anal. Calcd. for $C_{10}H_{11}N_3O_2S_2$: Found: | 44.59 44.80 | 4.12 4.16 | 15.60 15.53 | — — | — — |
| H | H | Cl | H | H | mp 140–140.5° C. (decomp.) | Anal. Calcd. for $C_9H_8ClN_3O_2S$: Found: | 37.31 37.50 | 2.78 2.97 | 14.50 14.68 | — — | — — |
| H | H | $OCH_3$ | H | H | mp 141.5° C. | Anal. Calcd. for $C_{10}H_{11}N_3O_3S_2$: Found: | 42.09 42.14 | 3.89 4.02 | 14.73 14.86 | — — | — — |
| i-Pr | H | i-Pr | H | i-Pr | mp 165–165.5° C. | Anal. Calcd. for $C_{18}H_{27}N_3O_2S_2$: Found: | 56.66 56.90 | 7.13 7.15 | 11.01 10.97 | — — | — — |
| Cl | H | H | H | Cl | mp 239–241° C. | Anal. Calcd. for $C_9H_7Cl_2N_3O_2S_2$: Found: | 33.34 33.14 | 2.18 2.12 | 12.96 12.91 | 21.87 21.73 | 19.78 19.62 |

TABLE II

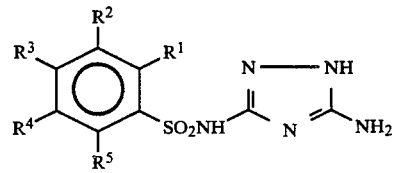

| $R^1$ | $R^2$ | $R^3$ | $R^4$ | $R^5$ | Physical Properties | Elemental Composition | C | H | N | Cl | S |
|---|---|---|---|---|---|---|---|---|---|---|---|
| H | H | H | H | H | mp 293° C.–294° C. | Anal. Calcd. for $C_8H_9N_5O_2S$: Found: | 40.16 40.29 | 3.79 3.67 | 29.27 29.40 | — — | 13.40 13.26 |
| $CF_3$ | H | H | H | H | mp 281° C.–283° C. (decomp.) | Anal. Calcd. for $C_9H_8F_3N_5O_2S$: Found: | 35.18 35.01 | 2.62 2.57 | 22.79 22.91 | — — | 10.44 10.22 |
| $NO_2$ | H | H | H | H | mp 255–256° C. (decomp.) | Anal. Calcd. for $C_8H_8N_6O_4S$: Found: | 33.80 34.11 | 2.84 2.79 | 29.57 29.35 | — — | 11.28 11.50 |
| Cl | H | H | H | H | mp 307–309° C. (decomp.) | Anal. Calcd. for $C_8H_8ClN_5O_2S$: Found: | 35.11 34.84 | 2.95 2.90 | 25.59 25.56 | 12.95 13.03 | 11.71 11.56 |
| $CH_3$ | H | H | H | H | mp 285–286° C. | Anal. Calcd. for $C_9H_{11}N_5O_2S$: Found: | 42.68 42.59 | 4.38 4.17 | 27.65 27.79 | — — | 12.66 12.46 |
| H | H | $CH_3$ | H | H | mp 314–315° C. | Anal. Calcd. for $C_9H_{11}N_5O_2S$: | 42.68 | 4.38 | 27.65 | — | — |

TABLE II-continued

| R¹ | R² | R³ | R⁴ | R⁵ | Physical Properties | Elemental Composition | C | H | N | Cl | S |
|---|---|---|---|---|---|---|---|---|---|---|---|
| | | | | | | Found: | 42.34 | 4.34 | 27.14 | — | — |
| H | H | Cl | H | H | mp 314–315° C. (decomp.) | Anal. Calcd. for $C_8H_8ClN_5O_2S$: | 35.11 | 2.95 | 25.59 | — | — |
| | | | | | | Found: | 34.90 | 3.12 | 25.30 | — | — |
| H | H | OCH₃ | H | H | mp 300° C. (decomp.) | Anal. Calcd. for $C_9H_{11}N_5O_3S$: | 40.14 | 4.12 | 26.01 | — | — |
| | | | | | | Found: | 40.10 | 4.25 | 25.72 | — | — |
| i-Pr | H | i-Pr | H | i-Pr | mp 314.5° C. (decomp.) | Anal. Calcd. for $C_{17}H_{27}N_5O_2S$: | 55.86 | 7.45 | 19.16 | — | — |
| | | | | | | Found: | 56.17 | 7.49 | 19.18 | — | — |
| Cl | H | H | H | Cl | mp 295–296° C. (decomp.) | Anal. Calcd. for $C_8H_7Cl_2N_5O_2S$: | 31.18 | 2.29 | 22.73 | 23.10 | 10.40 |
| | | | | | | Found: | 31.35 | 2.20 | 22.70 | 23.05 | 10.26 |
| F | H | H | H | F | mp 322–323° C. (decomp.) | Anal. Calcd. for $C_8H_7F_2N_5O_2S$: | 34.91 | 2.56 | 25.45 | — | — |
| | | | | | | Found: | 34.93 | 2.53 | 25.72 | — | — |
| Cl | Cl | H | H | H | mp 326–327° C. (decomp.) | Anal. Calcd. for $C_8H_7Cl_2N_5O_2S$: | 31.18 | 2.29 | 22.73 | 23.01 | 10.40 |
| | | | | | | Found: | 31.17 | 2.24 | 23.22 | 22.30 | 9.80 |

TABLE III

| R¹ | R² | R³ | R⁴ | R⁵ | Physical Properties | Elemental Composition | C | H | N | Cl | S |
|---|---|---|---|---|---|---|---|---|---|---|---|
| CF₃ | H | H | H | H | mp 246.5–248° C. | Anal. Calcd. for $C_{14}H_{12}F_3N_5O_2S$: | 45.28 | 3.26 | 18.86 | — | 8.71 |
| | | | | | | Found: | 45.31 | 3.33 | 18.74 | — | 8.71 |
| CF₃ | H | H | H | H | mp 202.5–203.5° C. | Anal. Calcd. for $C_{14}H_{15}N_5O_2S$: | 52.98 | 4.76 | 22.07 | — | 10.10 |
| | | | | | | Found: | 52.43 | 4.56 | 21.78 | — | 9.59 |
| NO₂ | H | H | H | H | mp 255–256° C. (decomp.) | Anal. Calcd. for $C_{13}H_{12}N_6O_4S$: | 44.83 | 3.47 | 24.13 | — | 9.20 |
| | | | | | | Found: | 44.88 | 3.34 | 24.51 | — | 9.09 |
| Cl | H | H | H | H | mp 216.5–219.5° C. | Anal. Calcd. for $C_{13}H_{12}ClN_5O_2S$: | 46.23 | 3.58 | 20.73 | 10.50 | 9.49 |
| | | | | | | Found: | 45.97 | 3.66 | 21.01 | 10.73 | 9.30 |
| H | H | CH₃ | H | H | mp 241–241.5° C. | Anal. Calcd. for $C_{14}H_{15}N_5O_2S$: | 52.98 | 4.76 | 22.07 | — | — |
| | | | | | | Found: | 52.70 | 4.96 | 22.02 | — | — |
| H | H | Cl | H | H | mp 254–255.5° C. | Anal. Calcd. for $C_{13}H_{12}ClN_5O_2S$: | 46.22 | 3.58 | 20.73 | — | — |
| | | | | | | Found: | 46.10 | 3.75 | 20.69 | — | — |
| H | H | OCH₃ | H | H | mp 198.5–199.5° C. | Anal. Calcd. for $C_{14}H_{15}N_5O_3S$: | 50.44 | 4.54 | 21.01 | — | — |
| | | | | | | Found: | 50.43 | 4.70 | 20.99 | — | — |
| i-Pr | H | i-Pr | H | i-Pr | mp 283° C. (decomp.) | Anal. Calcd. for $C_{22}H_{31}N_5O_2S$: | 61.51 | 7.27 | 16.30 | — | — |
| | | | | | | Found: | 61.30 | 7.33 | 16.28 | — | — |
| Cl | H | H | H | Cl | mp 259–261° C. | Anal. Calcd. for $C_{13}H_{11}Cl_2N_5O_2S$: | 41.95 | 2.98 | 18.81 | 19.05 | 8.61 |
| | | | | | | Found: | 41.86 | 2.94 | 19.09 | 18.92 | 8.39 |
| F | H | H | H | F | mp 261–262° C. | Anal. Calcd. for $C_{13}H_{11}F_2N_5O_2S$: | 46.02 | 3.27 | 20.64 | — | — |
| | | | | | | Found: | 45.94 | 3.19 | 20.79 | — | — |
| Cl | Cl | H | H | H | mp 231–233° C. | Anal. Calcd. for $C_{11}H_7Cl_2N_5O_2S$: | 41.95 | 2.98 | 18.81 | — | — |
| | | | | | | Found: | 41.83 | 2.90 | 19.55 | — | — |

TABLE IV

| R¹ | R⁵ | X | Y | Z | Physical Properties | Elemental Composition | C | H | N | Cl | S |
|---|---|---|---|---|---|---|---|---|---|---|---|
| Cl | H | H | Cl | H | mp 258.5– | Anal. Calcd. | | | | | |

TABLE IV-continued structure: pyrimidine with X, Y, Z substituents connected via N—N to triazole, connected to NHSO₂-phenyl with R¹ and R⁵ substituents

| R¹ | R⁵ | X | Y | Z | Physical Properties | Elemental Composition | C | H | N | Cl | S |
|---|---|---|---|---|---|---|---|---|---|---|---|
| | | | | | 260.5° C. | for $C_{11}H_7Cl_2N_5O_2S$: | 38.39 | 2.05 | 20.35 | 20.60 | 9.32 |
| | | | | | | Found: | 38.74 | 2.08 | 20.84 | 19.54 | 8.70 |
| Cl | H | $CH_3$ | Cl | $CH_3$ | mp 266–269° C. | Anal. Calcd. for $C_{13}H_{11}Cl_2N_5O_2S$: | 41.95 | 2.98 | 18.81 | 19.05 | 8.61 |
| | | | | | | Found: | 42.51 | 3.03 | 18.98 | 18.16 | 8.41 |
| Cl | H | $CF_3$ | H | $CH_3$ | mp 203–204.5° C. | Anal. Calcd. for $C_{13}H_9ClF_3N_5O_2S$: | 39.86 | 2.32 | 17.88 | 9.05 | 8.18 |
| | | | | | | Found: | 40.23 | 2.31 | 18.22 | 9.13 | 8.26 |
| Cl | H | $CF_3$ | H | $CF_3$ | mp 224–226° C. | Anal. Calcd. for $C_{13}H_6ClF_6N_5O_2S$: | 35.02 | 1.36 | 15.71 | 7.95 | 7.19 |
| | | | | | | Found: | 35.31 | 1.38 | 15.95 | 7.72 | 7.40 |
| Cl | H | H | $CH_3$ | H | mp 236–239° C. | Anal. Calcd. for $C_{12}H_{10}ClN_5O_2S$: | 44.52 | 3.11 | 21.63 | 10.95 | 9.90 |
| | | | | | | Found: | 44.17 | 3.05 | 21.93 | 11.01 | 9.69 |
| Cl | H | $CH_3$ | $CH_3$ | $CH_3$ | mp 273–280° C. | Anal. Calcd. for $C_{14}H_{14}ClN_5O_2S$: | 47.80 | 4.01 | 19.91 | 10.08 | 9.11 |
| | | | | | | Found: | 47.78 | 3.90 | 20.19 | 10.20 | 9.17 |
| Cl | H | $CH_2CH_3$ | H | $CH_2CH_3$ | mp 216–218° C. | Anal. Calcd. for $C_{15}H_{16}ClN_5O_2S$: | 49.25 | 4.41 | 19.14 | 9.69 | 8.76 |
| | | | | | | Found: | 49.18 | 4.36 | 19.45 | 9.64 | 8.75 |
| Cl | H | H | H | H | mp 253.5–256.5° C. | Anal. Calcd. for $C_{11}H_8ClN_5O_2S$: | 42.66 | 2.60 | 22.61 | 11.45 | 10.35 |
| | | | | | | Found: | 42.97 | 2.60 | 22.42 | 11.19 | 10.07 |
| Cl | H | $CH_3$ | H | H | mp 267.5–269° C. | Anal. Calcd. for $C_{12}H_{10}ClN_5O_2S$: | 44.52 | 3.11 | 21.63 | 10.95 | 9.90 |
| | | | | | | Found: | 44.36 | 3.07 | 21.69 | 10.82 | 10.15 |
| Cl | Cl | $CH_3$ | Cl | $CH_3$ | mp 296–297° C. | Anal. Calcd. for $C_{13}H_{10}Cl_3N_5O_2S$: | 38.39 | 2.48 | 17.22 | — | — |
| | | | | | | Found: | 38.48 | 2.44 | 17.58 | — | — |
| Cl | Cl | H | Cl | H | mp 262–264° C. | Anal. Calcd. for $C_{11}H_6Cl_3N_5O_2S$: | 34.89 | 1.60 | 18.50 | — | — |
| | | | | | | Found: | 34.72 | 1.78 | 19.12 | — | — |
| Cl | Cl | H | H | H | mp 264–269° C. | Anal. Calcd. for $C_{11}H_7Cl_2N_5O_2S$: | 38.38 | 2.05 | 20.35 | 20.61 | 9.32 |
| | | | | | | Found: | 38.29 | 2.05 | 20.08 | 19.80 | 9.13 |
| Cl | Cl | $CF_3$ | H | $CF_3$ | mp 238–240° C. | Anal. Calcd. for $C_{13}H_5F_6N_5O_2S$: | 32.51 | 1.05 | 14.59 | 14.77 | 6.68 |
| | | | | | | Found: | 32.19 | 1.01 | 14.57 | 14.51 | 6.86 |
| Cl | Cl | $CH_3$ | $CH_3$ | $CH_3$ | mp 347° C. (decomp.) | Anal. Calcd. for $C_{14}H_{13}Cl_2N_5O_2S$: | 43.53 | 3.39 | 18.13 | 18.35 | 8.30 |
| | | | | | | Found: | 43.52 | 3.29 | 18.42 | 18.37 | 8.29 |
| Cl | Cl | $CH_2CH_3$ | H | $CH_2CH_3$ | mp 259–261° C. | Anal. Calcd. for $C_{15}H_{15}Cl_2N_5O_2S$: | 45.01 | 3.78 | 17.50 | 17.72 | 8.01 |
| | | | | | | Found: | 44.44 | 3.72 | 17.79 | 17.33 | 8.32 |

TABLE V structure: thiophene with R¹, R², R³ substituents, SO₂NH-C(=N)-N=C(NH)NH₂

| R¹ | R² | R³ | Physical Properties | Elemental Composition | C | H | N | Cl | S | Br |
|---|---|---|---|---|---|---|---|---|---|---|
| H | H | Cl | mp 310° C. (decomp.) | Anal. Calcd. for $C_6H_6ClN_5O_2S_2$: | 25.76 | 2.16 | 25.04 | 12.68 | 22.93 | — |
| | | | | Found: | 25.81 | 2.13 | 25.18 | 12.40 | 22.17 | — |
| H | Br | Br | mp 325° C. (decomp.) | Anal. Calcd. for $C_6H_5Br_2N_5O_2S_2$: | 17.88 | 1.25 | 17.38 | — | 15.91 | 39.65 |
| | | | | Found: | 18.13 | 1.24 | 17.38 | — | 15.07 | 37.71 |

TABLE VI

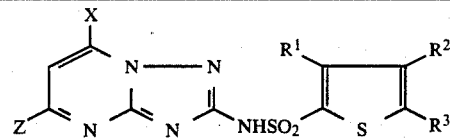

| R¹ | R² | R³ | X | Z | Physical Properties | Elemental Composition | C | H | N | Cl | S | Br |
|---|---|---|---|---|---|---|---|---|---|---|---|---|
| H | H | Cl | $CH_3$ | $CH_3$ | mp 200–202° C. | Anal. Calcd. for $C_{11}H_{10}ClN_5O_2S_2$: | 38.43 | 2.93 | 20.37 | 10.31 | 18.65 | — |
|  |  |  |  |  |  | Found: | 38.08 | 2.83 | 20.47 | 8.59 | 18.91 | — |
| H | Br | Br | $CH_3$ | $CH_3$ | mp 183–185° C. | Anal. Calcd. for $C_{11}H_9Br_2N_5O_2S_2$: | 28.28 | 1.94 | 14.99 | — | 13.73 | 34.21 |
|  |  |  |  |  |  | Found: | 28.06 | 1.78 | 14.97 | — | 13.90 | 33.60 |

What is claimed is:

1. Process for making a compound having the formula

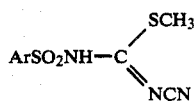

wherein Ar is phenyl which is substituted with from 1 to 5 substituents selected from halo, nitro, $C_1$–$C_4$ alkyl or alkoxy or $C_1$–$C_4$ mono- or polyfluoroalkyl or alkoxy, which comprises reacting a compound having the formula $ArSO_2NH_2$, wherein Ar is as above defined with dimethyl N-cyanodithioiminocarbonate in the presence of a tertiary amine or alkali metal hydroxide or alkoxide or an alkali metal carbonate in an organic solvent.

2. Process of claim 1 wherein the base is sodium hydroxide.

3. Process of claim 1 wherein the base is potassium carbonate.

4. Process of claim 1 wherein the solvent is acetone, methyl ethyl ketone, acetonitrile or tetrahydrofuran.

5. Process of claim 1 wherein the reaction is carried out at a temperature of from ambient temperature to reflux temperature.

* * * * *

UNITED STATES PATENT AND TRADEMARK OFFICE
CERTIFICATE OF CORRECTION

PATENT NO. : 4,650,892

DATED : March 17, 1987

INVENTOR(S) : William A. Kleschick, et al.

It is certified that error appears in the above-identified patent and that said Letters Patent is hereby corrected as shown below:

Column 1, under subtitle CROSS-REFERENCE TO RELATED APPLICATION line 8, "filed Jan. 14, 1985, pending." should read --filed Jan. 14, 1985, abandoned--.

Column 10, Table II, line 12, under subtitle N, "27.14" should read --27.44--.

Column 10, Table II, line 19, under subtitle Cl, "23.10" should read --23.01--.

Column 10, Table III, line 15, under subtitle S, "8.71" should read --8.63--.

Signed and Sealed this

Third Day of November, 1987

Attest:

DONALD J. QUIGG

Attesting Officer

Commissioner of Patents and Trademarks